(12) United States Patent  
Pajotin

(10) Patent No.: US 6,740,122 B1  
(45) Date of Patent: May 25, 2004

(54) PREFORMED CURVED PROSTHESIS THAT IS ADAPTED TO THE EXTERNAL ILIAC VESSELS

(75) Inventor: Philippe Pajotin, Cholet (FR)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/786,811

(22) PCT Filed: Sep. 10, 1999

(86) PCT No.: PCT/US99/20929

§ 371 (c)(1),
(2), (4) Date: Jul. 5, 2001

(87) PCT Pub. No.: WO00/15141

PCT Pub. Date: Mar. 23, 2000

(30) Foreign Application Priority Data

Sep. 11, 1999 (FR) .............................................. 9811332

(51) Int. Cl.⁷ ................................................. A61F 2/02
(52) U.S. Cl. ..................... 623/23.72; 606/151; 606/213
(58) Field of Search ........................... 623/23.72, 23.64; 606/215, 213, 151

(56) References Cited

U.S. PATENT DOCUMENTS

| | | |
|---|---|---|
| 2,671,444 A | 3/1954 | Pease |
| 3,559,214 A | 2/1971 | Pangman |
| 3,805,301 A | 4/1974 | Liebig |
| 3,875,928 A | 4/1975 | Angelchik |
| 3,988,411 A | 10/1976 | Capozza |

(List continued on next page.)

FOREIGN PATENT DOCUMENTS

| | | |
|---|---|---|
| AU | 593 267 B | 1/1988 |
| DE | 892 663 | 10/1953 |
| DE | 40 13 447 C1 | 2/1992 |
| DE | 92 12 261 U1 | 11/1993 |
| EP | 0 573 273 A2 | 12/1993 |
| EP | 0 592 244 A2 | 4/1994 |
| EP | 0 614 650 A2 | 9/1994 |
| EP | 0 836 838 A1 | 4/1998 |
| EP | 1 145 693 A2 | 10/2001 |
| FR | 2 682 284 A1 | 4/1993 |
| FR | 2 719 993 A1 | 11/1995 |
| FR | 2 735 015 A1 | 12/1996 |
| GB | 2 226 762 A | 7/1990 |
| JP | 5-329165 A2 | 12/1993 |
| JP | 700043 | 1/1995 |
| WO | WO 92/13500 A1 | 8/1992 |
| WO | WO 95/07666 A1 | 3/1995 |
| WO | WO 96/03091 A1 | 2/1996 |
| WO | WO 96/41588 A1 | 12/1996 |
| WO | WO 99/03422 A1 | 1/1999 |
| WO | WO 00/15142 A1 | 3/2000 |
| WO | WO 00/42943 A1 | 7/2000 |
| WO | WO 01/15625 A1 | 3/2001 |
| WO | WO 01/80773 A1 | 11/2001 |

*Primary Examiner*—Corrine McDermott
*Assistant Examiner*—Thomas J Sweet

(57) ABSTRACT

A prosthesis is provided for repairing a defect in a muscle or tissue wall. The prosthesis has a preformed shape that conforms to the wall to facilitate placement and minimize shifting of the prosthesis when positioned on the wall. The prosthesis may include a body formed of a sheet of surgical mesh fabric having a flexible body surrounded by a peripheral edge that may be welded or fused so that the body is capable of resuming the preformed shape after being temporarily deformed to allow for implantation. The body is adapted to the inclination of the external iliac vessels. In one embodiment, the body includes a first portion configured with a shape of a cap and a second portion with a substantially spherical shape that is connected to the first portion at the lower edge thereof. The first portion has a first radius of curvature and the second portion has a second radius of curvature that is less than the first radius of curvature. The second portion includes an outer edge that forms an angle with the lower edge of the first portion that is greater than 100° at the apex of the prosthesis.

16 Claims, 1 Drawing Sheet

U.S. PATENT DOCUMENTS

| | | |
|---|---|---|
| 4,345,414 A | 8/1982 | Bornat et al. |
| 4,403,604 A | 9/1983 | Wilkinson |
| 4,441,215 A | 4/1984 | Kaster |
| 4,545,082 A | 10/1985 | Hood |
| 4,555,378 A | 11/1985 | Martin et al. |
| 4,573,999 A | 3/1986 | Netto |
| 4,693,720 A | 9/1987 | Scharnberg et al. |
| 4,728,328 A | 3/1988 | Hughes et al. |
| 4,841,948 A | 6/1989 | Bauer et al. |
| 5,061,277 A | 10/1991 | Carpentier et al. |
| 5,112,352 A | 5/1992 | Novack |
| 5,116,370 A | 5/1992 | Foglietti |
| 5,146,933 A | 9/1992 | Boyd |
| 5,147,398 A | 9/1992 | Lynn et al. |
| 5,236,454 A | 8/1993 | Miller |
| 5,258,000 A | 11/1993 | Gianturco |
| 5,292,328 A | 3/1994 | Hain et al. |
| 5,306,296 A | 4/1994 | Wright et al. |
| 5,356,429 A | 10/1994 | Seare |
| 5,356,432 A | 10/1994 | Rutkow et al. |
| 5,366,460 A | 11/1994 | Eberbach |
| 5,383,477 A | 1/1995 | DeMatteis |
| 5,383,925 A | 1/1995 | Schmitt |
| 5,443,508 A | 8/1995 | Giampapa |
| 5,456,720 A | 10/1995 | Schultz et al. |
| 5,466,258 A | 11/1995 | Rubin |
| 5,584,884 A | 12/1996 | Pignataro |
| 5,593,441 A | 1/1997 | Lichtenstein et al. |
| 5,674,279 A | 10/1997 | Wright et al. |
| 5,676,146 A | 10/1997 | Scarborough |
| 5,695,525 A | 12/1997 | Mulhauser et al. |
| 5,702,459 A | 12/1997 | Hummer et al. |
| 5,716,404 A | 2/1998 | Vacanti et al. |
| 5,716,408 A | 2/1998 | Eldridge et al. |
| 5,725,577 A | 3/1998 | Saxon |
| 5,743,917 A | 4/1998 | Saxon |
| 5,766,246 A | 6/1998 | Mulhauser et al. |
| 5,769,864 A | 6/1998 | Kugel |
| 5,796,462 A | 8/1998 | Roffman et al. |
| 5,865,728 A | 2/1999 | Moll et al. |
| 5,895,424 A | 4/1999 | Steele, Sr. et al. |
| 5,954,767 A | 9/1999 | Pajotin et al. |
| 6,004,333 A | 12/1999 | Sheffield et al. |
| 6,024,763 A | 2/2000 | Lenker et al. |
| 6,042,592 A | 3/2000 | Schmitt |
| 6,066,776 A | 5/2000 | Goodwin et al. |
| 6,066,777 A | 5/2000 | Benchetrit |
| 6,074,419 A | 6/2000 | Healy et al. |
| 6,090,116 A | 7/2000 | D'Aversa et al. |
| 6,096,044 A | 8/2000 | Boyd et al. |
| 6,113,623 A | 9/2000 | Sgro |
| 6,120,434 A | 9/2000 | Kimura et al. |
| 6,120,539 A | 9/2000 | Eldridge et al. |
| 6,162,962 A | 12/2000 | Hinsch et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,214,020 B1 | 4/2001 | Mulhauser et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,280,453 B1 | 8/2001 | Kugel et al. |
| 6,287,293 B1 | 9/2001 | Jones et al. |
| 6,287,316 B1 | 9/2001 | Agarwal et al. |
| 6,290,708 B1 | 9/2001 | Kugel et al. |
| 6,306,154 B1 | 10/2001 | Hudson et al. |
| 6,312,442 B1 | 11/2001 | Kieturakis et al. |
| 6,312,456 B1 | 11/2001 | Kranz et al. |
| 6,319,264 B1 | 11/2001 | Törmälä et al. |
| 6,368,541 B1 | 4/2002 | Pajotin et al. |
| 6,451,139 B1 | 9/2002 | Weber-Unger et al. |
| 2001/0027347 A1 | 10/2001 | Rousseau |
| 2001/0034528 A1 | 10/2001 | Foerster et al. |
| 2001/0049538 A1 | 12/2001 | Trabucco |
| 2001/0049539 A1 | 12/2001 | Rehil |
| 2001/0053919 A1 | 12/2001 | Kieturakis et al. |

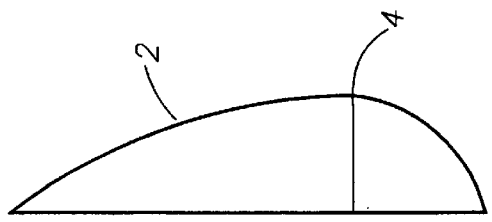
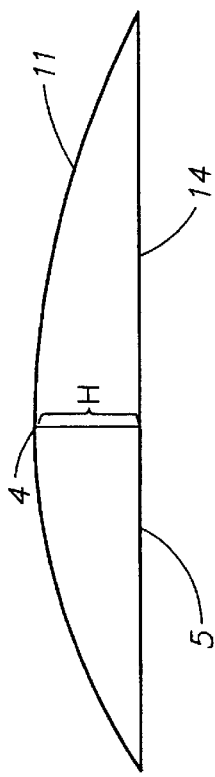
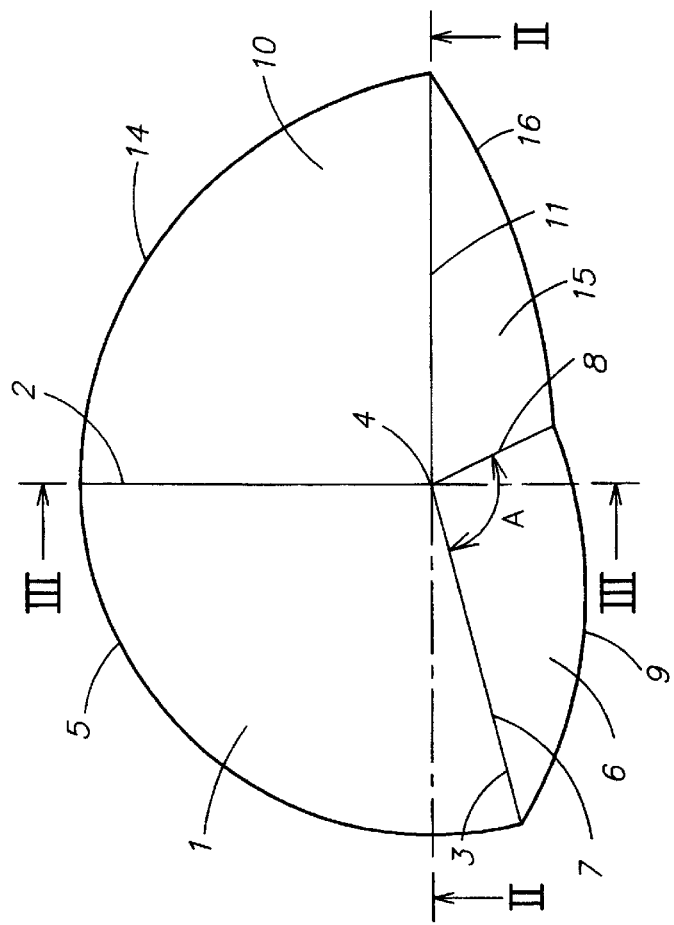
FIG. 3
FIG. 2
FIG. 1

PREFORMED CURVED PROSTHESIS THAT IS ADAPTED TO THE EXTERNAL ILIAC VESSELS

RELATED APPLICATIONS

This application is a national stage filing under 35 U.S.C. §371 of PCT International application PCT/US99/20929, filed Sep. 10, 1999, which was published in English under PCT Article 21(2).

Foreign priority benefits are claimed under 35 U.S.C. §119(a)–(d) or 35 U.S.C. §365(b) to French application number 98/11332, filed Sep. 11, 1998.

BACKGROUND OF THE INVENTION

1. Field of the Invention

The present invention relates to an implantable prosthesis, and more particularly to a prosthesis for repairing a hernia.

2. Description of the Related Art

A defect in a muscle or tissue wall, such as a hernia, is commonly repaired with an implantable prosthesis that is configured to cover and/or fill the defect. In many instances, a flat sheet of an implantable, non-resorbable, flexible mesh material, such as BARD MESH, has been employed for the parietal repair of hernias and eventrations of the abdominal wall. However, a surgeon may experience some difficulty positioning the mesh between the parietal peritoneum and the abdominopelvic wall. The mesh may also fold or wrinkle and be difficult to maintain in position.

Applicant previously developed an implantable prosthesis for repairing a defect in a muscle or tissue wall to alleviate some of these concerns. The prosthesis, which is disclosed in WO 95/07666 and is assigned to C. R. Bard, the assignee of the present application, is made of an implantable, nonabsorbable and flexible material that is formed to independently assume a curved shape adapted to conform to the anatomical shape of the wall. The prosthesis includes a body comprised of a first portion formed in the shape of a cap and a second portion having a substantially spherical shape connected to a lower edge of the first portion. The second portion has a radius of curvature that is less than the radius of curvature of the first portion. The second portion includes an outer edge that meets the lower edge of the first portion at the apex of the body, which is the highest point of the curved prosthesis.

This prosthesis has proven useful and has become established in the practice of muscle or tissue wall repair in the inguinofemoral region. The prosthesis is not subject to stresses when deformed and, therefore, has no tendency to shift upon implantation. The prosthesis reinforces the abdominal wall at the anatomical region of concern.

It has nevertheless been observed that the reinforcement of the abdominal wall offered by the prosthesis could be extended.

It is an object of the present invention to provide an improved prosthesis for repairing a defect in a muscle or tissue wall by configuring the prosthesis with regard to certain anatomical zones.

SUMMARY OF THE INVENTION

The present invention is an implantable prosthesis for repairing a defect in a muscle or tissue wall. The prosthesis includes a body of prosthetic material having a preformed three-dimensional contoured shape that independently assumes a curved shape adapted to conform to the wall. The body is configured to adapt to the inclination of the external iliac vessels to facilitate a desired placement of the prosthesis when employed for repairing an inguinal hernia.

According to one embodiment of the invention, the body includes a first portion with a first lower edge and a second portion with a second outer edge, the second portion being connected to the first portion at the first lower edge. The first portion is configured to have a shape of a cap and the second portion is configured with a substantially spherical shape. The first portion has a first radius of curvature and the second portion has a second radius of curvature that is less than the first radius of curvature. The second outer edge and the first lower edge meet at an apex of the body, the second outer edge forming an angle with the first lower edge that is greater than approximately 100° at the apex.

According to one aspect of the invention, the angle is between approximately 101° and approximately 120°.

According to another aspect of the invention, the first portion includes a first outer edge and the second portion includes a second outer edge, and the body further includes a third portion with a third lower edge and a fourth portion. The third portion is connected to the first outer edge and the fourth portion is connected to the third lower edge and to the second outer edge.

A depression may be formed between the second and fourth portions which is configured to be placed proximate the external iliac vessels when the prosthesis is positioned on a wall to repair an inguinal hernia. The angular orientation between the first lower edge and the second outer edge and the depression between the second and fourth portions are adapted to the inclination of the external iliac vessels to facilitate placement of and to minimize shifting of the prosthesis when positioned on the wall. The angular orientation and the depression also provide a degree of deformation for matching adjacent contours.

According to a further aspect of the invention, the prosthesis is configured with a ratio of the surface area of the third portion to the total surface area of the prosthesis from approximately 0.25 to approximately 0.40.

According to still another aspect of the invention, the third portion has a third radius of curvature that is substantially equal to the first radius of curvature along the first outer edge. This configuration reduces the incidence of wrinkles or folds occuring between the first portion and the third portion so that the first and third portions do not partially cover each other upon or after implantation, thereby ensuring that the overall size of the prosthesis is sufficient to adequately cover the desired portion of the wall.

BRIEF DESCRIPTION OF THE DRAWINGS

The foregoing and other objects and advantages of the invention will be appreciated more fully from the following drawings, given solely by way of example, in which:

FIG. 1 is a plan view of a prosthesis according to one illustrative embodiment of the invention;

FIG. 2 is a cross-sectional view of the prosthesis taken along section line II-II in FIG. 1; and FIG. 3 is a cross-sectional view of the prosthesis taken along section line III-III in FIG. 1.

DETAILED DESCRIPTION

FIGS. 1–3 illustrate one embodiment of a prosthesis for repairing a defect in a muscle or tissue wall, such as a hernia. The prosthesis includes a body of prosthetic material that is preformed with a three-dimensional configuration that conforms to the anatomical shape of the defective wall to facilitate placement and minimize shifting of the prosthesis when positioned on the wall. The body includes a plurality of shaped portions that are joined to each other to create a desired configuration. The particular orientation between several portions of the body is adapted to the inclination of the external iliac vessels to facilitate a desired placement of the prosthesis when employed for repairing an inguinal hernia.

In one illustrative embodiment, the body includes first, second, third and fourth portions 1, 6, 10, 15, respectively, that are connected to each other to form a unitary structure. Each of the portions includes a curved surface that provide the prosthesis with the preformed contoured shape.

The first portion 1 is formed with a substantially spherical shape and includes a first outer edge 2 and a first lower edge 3 joined to each other at an apex 4 of the prosthesis, which is the highest point thereof. The first portion 1 also includes a circular inner edge 5 that extends in the same plane as the outer and lower edges 2, 3.

The second portion 6 is disposed below the first portion 1 and includes an upper edge 7, a second outer edge 8 and a curved second lower edge 9. As shown, the upper edge 7 merges with the first lower edge 3 of the first portion.

The first and second portions 1, 6 are configured with an angle A at the apex 4 between the first lower edge 3 and the second outer edge 8 that positions the second outer edge 8 substantially opposite the external iliac vessels when implanted to repair an inguinal hernia. In one embodiment, the angle A is greater than 100° with an illustrative range of approximately 101° to 120°.

The third portion 10, which lies adjacent the first portion 1, includes a third lower edge 11 and a circular third outer edge 14. The third portion 10 is connected to the first portion 1 along the first outer edge 2.

The fourth portion 15 is positioned below the third portion 10 and adjacent the second portion 6. The fourth portion 15 is defined by and is connected to the third lower edge 11 of the third portion 10 and the second outer edge 8 of the second portion 6. The fourth portion also includes a curved fourth lower edge 16.

As illustrated in FIG. 1, the inner edge 5, the third outer edge 14 and the second and fourth lower edges 9, 16 form a generally D-shaped peripheral edge of the prosthesis. The peripheral edge may be welded or fused so that the body can regain its contoured shape after being deformed during implantation.

Each of the second and fourth portions 6, 15 may also have substantially spherical shapes to enhance conformance to a particular anatomical shape. In one illustrative embodiment, the radius of curvature of the second and fourth portions is less than the radius of curvature of the first portion to form surfaces in the second and fourth portions that have a steeper incline relative to the first portion.

The second and fourth portions are shaped to form a depression in the surface of the body that is configured to receive the external iliac vessels when the prosthesis is employed for inguinal hernia repair. The depression extends inwardly from the peripheral edge between the second and fourth lower edges 9, 16 toward the apex 4.

The particular angular orientation between the first lower edge 3 and the second outer edge 8 and the depression between the second and fourth portions 6, 15 are adapted to the inclination of the external iliac vessels to facilitate placement of and to minimize shifting of the prosthesis when positioned on the wall. The angular orientation and the depression also provide a degree of deformation for matching adjacent contours.

The prosthesis may also be configured to substantially reduce the incidence of wrinkles or folds between the first and third portions so that the first and third portions do not partially cover each other upon or after implantation, thereby ensuring that the overall size of the prosthesis is sufficient to adequately cover the desired portion of the wall. In one illustrative embodiment, the first portion 1 has a first radius of curvature and the third portion 14 has a third radius of curvature that is substantially equal to the first radius of curvature along the first outer edge 2.

The prosthesis may be formed from an implantable, biologically compatible material that is nonabsorbable and flexible. In one embodiment, the prosthesis is formed of a knitted fabric of implantable polypropylene filament, such as BARD MESH, that includes a plurality of interstices (not shown) for promoting tissue ingrowth to the prosthesis. It is to be understood, however, that the prosthesis may be formed of any suitable material.

The prosthesis may be configured to have any shape and size suitable for a particular application. In one embodiment, the height H of the prosthesis from a plane defined by the peripheral edge and the apex 4 is approximately 21 mm. The first portion 1 has a substantially spherical shape with a radius of curvature of approximately 120 mm, particularly along the first outer edge 2. The third portion 10 has substantially the same radius of curvature of approximately 120 mm adjacent the first outer edge 2. The second and fourth portions 6, 15 each has a substantially spherical shape with a radius of curvature of approximately 35 mm. The total surface area of the prosthesis is approximately 44,780 mm$^2$, with the second portion 10 having a surface area of approximately 12,735 mm$^2$.

The disclosed configuration is particularly suited for repairing an inguinal hernia. It is to be appreciated, however, that this configuration is exemplary and that the prosthesis may be configured to have other shapes and sizes suitable for a particular application.

The preformed curved shape of the prosthesis may be obtained using any suitable manufacturing process. In one illustrative embodiment, the prosthesis is fabricated using a thermoforming procedure that includes placing a sheet of mesh fabric in a mold having the desired shape for the prosthesis, heating the fabric in the mold at an approximate temperature of 100° C. to 200° C. for a period of approximately 5 to 60 minutes, and subsequently cooling the fabric in the mold with an air flow having an approximate temperature of 15° C. to 30° C. for a period of approximately 5 to 60 minutes.

The edges of the prosthesis may be welded by fusing the meshes and the material using an ultrasonic welding procedure. During this procedure, the prosthesis is maintained between an element generating vibrations and an anvil that is configured to the particular dimensions of the prosthesis. In one embodiment, the edges are welded at a pressure of approximately 150 kPa to 800 kPa and an energy of approximately 100 to 5000 joules for a period of approximately 50 to 5000 milliseconds.

Once the sheet of mesh fabric has been shaped and the edges of the shaped prosthesis have been welded, any excess fabric extending beyond the welded edges is separated from the body of the prosthesis using a manual cutting procedure to form the completed prosthesis.

After inspection, the prosthesis may be packed in an internal packing (shell and insert) that has been designed specifically according to the three-dimensional characteristics of the prosthesis so as to comply with and protect the preformed curved shape of the prosthesis. The internal packing may be subsequently placed and packaged in a external packing for additional protection. The entire assembly may then be sterilized using any suitable method, such as with ethylene oxide, to provide a sterile prosthesis that is ready for implantation.

It should be understood that the foregoing description of the invention is intended merely to be illustrative thereof and that other embodiments, modifications, and equivalents of the invention are within the scope of the invention recited in the claims appended hereto.

What is claimed is:

1. An implantable prosthesis for repairing a defect in a muscle or tissue wall, the prosthesis comprising:
   a body of prosthetic material having a preformed three-dimensional contoured shape that independently assumes a curved shape adapted to conform to the wall, the body including a first portion with a first lower edge and a second portion with a second outer edge, the second portion being connected to the first portion at the first lower edge, the first portion configured to have a shape curved in three dimensions and the second portion configured with a substantially spherical-shaped surface, the first portion having a first radius of curvature and the second portion having a second radius of curvature that is less than the first radius of curvature, the second outer edge and the first lower edge meeting at an apex of the body, the second outer edge forming an angle with the first lower edge that is greater than approximately 100° at the apex.

2. The prosthesis according to claim 1, wherein the angle is between approximately 101° and approximately 120°.

3. The prosthesis according to claim 1, wherein the first portion includes a first outer edge, and wherein the body further includes a third portion with a third lower edge and a fourth portion, the third portion being connected to the first outer edge and the fourth portion being connected to the third lower edge and to the second outer edge.

4. The prosthesis according to claim 3, wherein the third portion has a surface area and the body has a total surface area, the prosthesis being configured with a ratio of the surface area of the third portion to the total surface area that ranges from approximately 0.25 to approximately 0.40.

5. The prosthesis according to claim 3, wherein the third portion has a third radius of curvature that is substantially equal to the first radius of curvature along the first outer edge.

6. The prosthesis according to claim 4, wherein the total surface area is greater than approximately 40,000 mm$^2$.

7. The prosthesis according to claim 3, wherein the fourth portion is configured with a substantially spherical-shaped surface.

8. The prosthesis according to claim 3, wherein the body includes a permanent depression between the second portion and the fourth portion, the depression being constructed and arranged to be placed proximate the external iliac vessels when the prosthesis is positioned on the wall to repair an inguinal hernia.

9. The prosthesis according to claim 8, wherein the depression extends inwardly from a peripheral edge of the body toward the apex.

10. The prosthesis according to claim 3, wherein the fourth portion has a fourth radius of curvature that is substantially equal to the second radius of curvature.

11. The prosthesis according to claim 3, wherein each of the second and fourth portions includes a curved lower edge.

12. The prosthesis according to claim 1, wherein the body includes a peripheral edge that is generally D-shaped.

13. The prosthesis according to claim 1, wherein the first radius of curvature is approximately 120 mm.

14. The prosthesis according to claim 1, wherein the second radius of curvature is approximately 35 mm.

15. The prosthesis according to claim 1, wherein the body of prosthetic material includes surgical mesh.

16. The prosthesis according to claim 1, wherein the first portion is configured with a substantially spherical-shaped surface.

* * * * *